US011672455B2

(12) United States Patent
Zhang et al.

(10) Patent No.: US 11,672,455 B2
(45) Date of Patent: Jun. 13, 2023

(54) ALERT VERSUS FATIGUE DISCRIMINATOR

(71) Applicant: Agency for Science Technology And Research, Singapore (SG)

(72) Inventors: Zhuo Zhang, Singapore (SG); Aung Aung Phyo Wai, Singapore (SG); Cuntai Guan, Singapore (SG); Hai Hong Zhang, Singapore (SG)

(73) Assignee: Agency for Science Technology And Research, Singapore (SG)

( * ) Notice: Subject to any disclaimer, the term of this patent is extended or adjusted under 35 U.S.C. 154(b) by 177 days.

(21) Appl. No.: 16/957,073

(22) PCT Filed: Dec. 29, 2017

(86) PCT No.: PCT/SG2017/050655
§ 371 (c)(1),
(2) Date: Jun. 22, 2020

(87) PCT Pub. No.: WO2019/132768
PCT Pub. Date: Jul. 4, 2019

(65) Prior Publication Data
US 2020/0337622 A1 Oct. 29, 2020

(51) Int. Cl.
*A61B 5/16* (2006.01)
*A61B 5/18* (2006.01)
(Continued)

(52) U.S. Cl.
CPC .............. *A61B 5/165* (2013.01); *A61B 5/18* (2013.01); *A61B 5/316* (2021.01); *A61B 5/369* (2021.01);
(Continued)

(58) Field of Classification Search
CPC .......... A61B 5/165; A61B 5/369; A61B 5/316; A61B 5/18; A61B 5/7267; A61B 5/163; A61B 5/374; A61B 5/0006
See application file for complete search history.

(56) References Cited

U.S. PATENT DOCUMENTS 6,625,485 B2    9/2003 Levendowski et al.
2015/0223743 A1    8/2015 Pathangay et al.

FOREIGN PATENT DOCUMENTS

CN    102274032 A  *  12/2011
CN    102274032 A     12/2011
CN    103919565 A     7/2014

OTHER PUBLICATIONS

Rosipal, R. et al., "EEG-Based Drivers' Drowsiness Monitoring Using a Hierarchical Gaussian Mixture Model," International Conference on Foundations of Augmented Cognition, Jul. 31, 2007, pp. 294-303 [Retrieved on Feb. 8, 2018] <DOI: 10.1007/978-3-540-73216-7_33> p. 295 Introduction, pp. 296-297 Karolinska Drowsiness Scoring Method, Hierarchical Gaussian Mixture Model, pp. 298-299 Experiments, p. 301 Study B.
(Continued)

*Primary Examiner* — Robert J Michaud
(74) *Attorney, Agent, or Firm* — Potomac Law Group, PLLC; John J. Penny, Jr.

(57) ABSTRACT

Described is a computer system for establishing an electroencephalogram (EEG) model for discriminating between alert and fatigue states. The computer system comprises a receiver module for receiving an alert state segment illustrative of an alert state of at least one subject, and one or more EEG fatigue data segments illustrative of a fatigue state of the at least one subject. The computer system further comprises a segment selector for selecting one of the one or more fatigue data segments and setting it to be an assumed maximum fatigue segment, an EEG classifier trainer for training an EEG classifier by extracting an EEG feature space from the alert state segment and assumed maximum
(Continued)

fatigue segment, and a maximum fatigue identifier module for identifying a segment of maximum fatigue by applying the EEG classifier to each of the fatigue data segments. The computer system further comprises a segment comparator for determining if the segment of maximum fatigue is consistent with the assumed maximum fatigue segment, and a limit setter for setting the segment of maximum fatigue as a revised assumed maximum fatigue segment, if the segment of maximum fatigue is inconsistent with the assumed maximum fatigue segment, and supplying the EEG classifier trainer with the revised assumed maximum fatigue segment. The computer system further comprises a model output module for setting the EEG classifier as the EEG model for discriminating between alert and fatigue states in segments of EEG data, if the segment of maximum fatigue is consistent with the assumed maximum fatigue segment.

18 Claims, 8 Drawing Sheets

(51) Int. Cl.
*A61B 5/00* (2006.01)
*A61B 5/316* (2021.01)
*A61B 5/369* (2021.01)
*A61B 5/374* (2021.01)

(52) U.S. Cl.
CPC .......... *A61B 5/7267* (2013.01); *A61B 5/0006* (2013.01); *A61B 5/163* (2017.08); *A61B 5/374* (2021.01)

(56) References Cited

OTHER PUBLICATIONS

Hu, S. et al., "Driver fatigue detection from electroencephalogram spectrum after electrooculography artefact removal," IET Intelligent Transport Systems, Jul. 16, 2014, vol. 7, No. 1, pp. 105-113 [Retrieved on Feb. 8, 2018]<DOI: 10.1049/IET-ITS.2012.0045> Whole document.
International Search Report and Written Opinion issued in connection with International Application No. PCT/SG2017/050655 dated Mar. 26, 2018.

* cited by examiner

Sensors
EEG (Muse headband)
Eye Tracker (Tobii EyeX)
Camera (Kinect v2)

Data Collection Time
- 9:30 am
- 1:30 pm
- 4:00 pm

Target No. of Subjects: 30
Experiment time: ~1.5 hr

Instructions to Subject
Pay full attention to the screen.
React as fast as possible.
Minimize eye/head movements and blinks.
Informed of car deviation only in 'left direction'.

Game Parameters
Car-Deviation Inter-stimulus Interval: 5-10 s
K.S.S survey timeout: 10 min

Driving Instruction
Place both arms on the wheel all the time. Allow to pause the game for any event necessary to do so. Minimize head, eyes or body movements during driving.

Instructions to Experimenter
- Check Eye Tracker's accuracy enabling 'Gaze Bubble' and ask subjects moving eyes around the screen (corners, middle)
- Check EEG's signal quality asking subject to perform eye blinks, others, etc.
- Check Kinect's outputs looking at both RGB and Depth outputs

Figure. 6

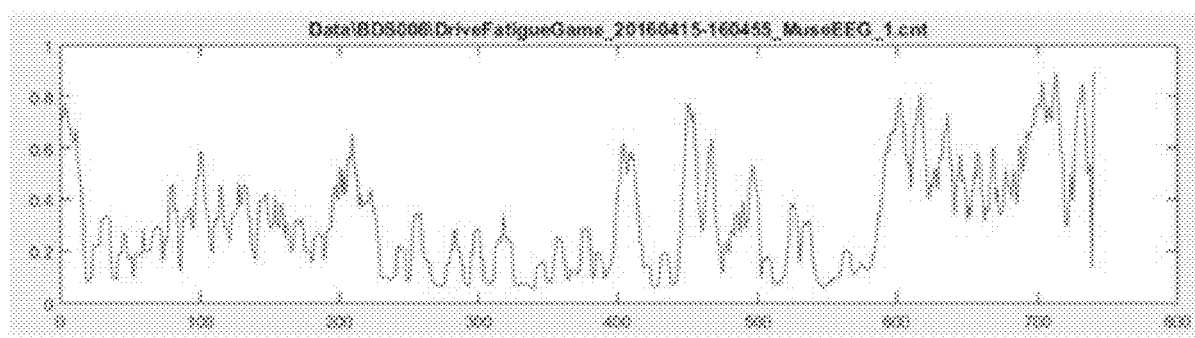
(a)
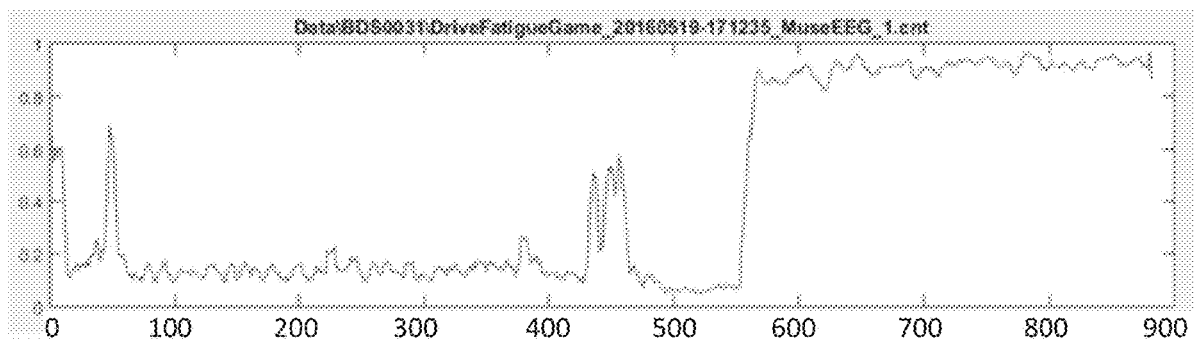
(b)
Figure. 7

ALERT VERSUS FATIGUE DISCRIMINATOR

TECHNICAL FIELD

The present disclosure relates to a computer system for establishing an alert versus fatigue discriminator. The present disclosure further relates to a computer process implemented by such a computer system.

BACKGROUND

Driver fatigue is one of the major contributors to road traffic accidents. Driver fatigue detection thus plays an important role in ensuring traffic safety.

In order to determine whether somebody is experiencing fatigue, it is useful to distinguish neuro-physiological symptoms inferring fatigue from those inferring an alert state. The different neuro-physiological symptoms are assessed during controlled tests (e.g. in front of a display), designed with sufficient length that the tests are assumed to induce fatigue. Then various methods are employed to categorise fatigue states of the driver based on the measurements taken during the tests The majority of the fatigue studies employ objective measurement involving displaying a scene on a display in which the user or driver is driving. Such measurements may be of driver behavioural performance—e.g. duration of responses to events such as lane deviation of another vehicle—driver physical state—e.g. eyes closing over several consecutive frames, are a combination thereof.

Subjective methods have also been proposed, requiring drivers to self-rate their fatigue levels. However, such measurements are limited by the fact that each individual must exercise their own judgement on the fatigue levels.

In fatigue inducing experiments, signals are measured—e.g. heart rate, respiratory rate, etc—and assumptions are made as to when fatigue is likely to have onset. Typically, the midpoint of a test is deemed illustrative of a driver's transition from an alert state to a fatigue state. Thus signals recorded after that time is deemed to be illustrative of fatigue. Thus such techniques rely on a subject descending into fatigue over the course of the test in a substantially linear fashion. If the test is too long, or not long enough, the linear descension from alert to fatigue is inaccurate.

It is also common that a subject will fluctuate between alert states and fatigue states, before descending into a persistent state of fatigue. If the subject is in an alert state for a period including the mid-point of the test, then the baseline used to discriminate between alert states and fatigue states may result in the subject subsequently being assumed to be in a fatigue when in fact they are in an alert state. Conversely, if the subject is at their most fatigued for a period including the mid-point of the test, then the baseline used to discriminate between alert states and fatigue states may result in the subject subsequently being assumed to be in an alert state when in fact they are in the preliminary stages of fatigue.

It is desirable therefore to provide a mechanism for discriminating between alert and fatigue states that overcomes or ameliorates one or more of the abovementioned disadvantages with known methods.

SUMMARY

In accordance with the present disclosure there is provided a computer system for establishing an electroencephalogram (EEG) model for discriminating between alert and fatigue states, comprising: a receiver module for receiving:
  an alert state segment illustrative of an alert state of at least one subject; and
  one or more EEG fatigue data segments illustrative of a fatigue state of the at least one subject;
a segment selector for selecting one of the one or more fatigue data segments and setting it to be an assumed maximum fatigue segment;
an EEG classifier trainer for training an EEG classifier by extracting an EEG feature space from the alert state segment and assumed maximum fatigue segment;
a maximum fatigue identifier module for identifying a segment of maximum fatigue by applying the EEG classifier to each of the fatigue data segments;
a segment comparator for determining if the segment of maximum fatigue is consistent with the assumed maximum fatigue segment;
a limit setter for:
  setting the segment of maximum fatigue as a revised assumed maximum fatigue segment, if the segment of maximum fatigue is inconsistent with the assumed maximum fatigue segment; and
  supplying the EEG classifier trainer with the revised assumed maximum fatigue segment; and
a model output module for setting the EEG classifier as the EEG model for discriminating between alert and fatigue states in segments of EEG data, if the segment of maximum fatigue is consistent with the assumed maximum fatigue segment.

The computer system may further comprise a discriminator system configured to apply the EEG model to determine if one or more subsequently recorded EEG segments are each representative of a fatigue state or an alert state.

The EEG classifier may be configured to extract the EEG feature space on the basis that the alert state segment and assumed maximum fatigue segment define respectively opposite ends of a fatigue spectrum. The EEG classifier may further be configured to extract the EEG feature space by calculating spectral power ratios for the alert state segment and assumed maximum fatigue segment. The EEG classifier may further be configured to extract the EEG feature space by calculating spectral envelopes for the alert state segment and assumed maximum fatigue segment. The spectral envelopes may be calculated from the spectral power ratios. The EEG classifier may be configured to calculate Gaussian parameters for the spectral power ratios and spectral envelopes.

The maximum fatigue identifier may comprise a scorer configured to determine a score for each of the one or more EEG fatigue data segments, and the segment comparator may be configured to determine that the maximum fatigue is inconsistent with the assumed maximum fatigue segment if:
  the score for the segment of maximum fatigue is greater than that for the assumed maximum fatigue segment; or
  the score for the segment of maximum fatigue is greater than the score for the assumed maximum fatigue segment by at least a predetermined amount.

The computer system may further comprise a segmenter, the receiver module being configured to receive the one or more EEG fatigue data segments by receiving a period of EEG fatigue data and segmenting the EEG fatigue data into the one or more EEG fatigue data segments using the segmenter. The segmenter may be configured to segment the EEG fatigue data overlapping segments, a first half of each segment overlapping a preceding segment and a latter half of each segment overlapping a succeeding segment.

The present disclosure further provides a computer process for establishing an electroencephalogram (EEG) model for discriminating between alert and fatigue states, comprising:

i. receiving:
   an alert state segment illustrative of an alert state of at least one subject; and
   one or more EEG fatigue data segments illustrative of a fatigue state of the at least one subject;
ii. selecting one of the one or more fatigue data segments and setting it to be an assumed maximum fatigue segment;
iii. training an EEG classifier by extracting an EEG feature space from the alert state segment and assumed maximum fatigue segment;
iv. identifying a segment of maximum fatigue by applying the EEG classifier to each of the fatigue data segments;
v(1). if the segment of maximum fatigue is inconsistent with the assumed maximum fatigue segment:
   setting the segment of maximum fatigue as the assumed maximum fatigue segment; and
   performing steps iii. to v.; and
v(2). if the segment of maximum fatigue is consistent with the assumed maximum fatigue segment, setting the EEG classifier as the EEG model for discriminating between alert and fatigue states in EEG data.

A length of the alert state segment and the assumed maximum fatigue segment may be the same. The EEG feature space may be produced based on the alert state segment and assumed maximum fatigue segment defining respectively opposite ends of a fatigue spectrum. The EEG feature space may be based on spectral power ratios for the alert state segment and assumed maximum fatigue segment. The EEG feature space may be based on spectral envelopes for the alert state segment and assumed maximum fatigue segment. The spectral envelopes may be calculated from the spectral power ratios.

The EEG classifier may be used to determine a score for each of the one or more EEG fatigue data segments, and the maximum fatigue is inconsistent with the assumed maximum fatigue segment if:
   the score for the segment of maximum fatigue is greater than that for the assumed maximum fatigue segment; or
   the maximum fatigue is greater than the assumed maximum fatigue segment by at least a predetermined amount.

Receiving one or more EEG fatigue data segments may comprise receiving a period of EEG data and segmenting the EEG fatigue data into the one or more EEG fatigue data segments. Segmenting the EEG fatigue data into the one or more EEG fatigue data segments may comprise segmenting the EEG fatigue data into overlapping segments, a first half of each segment overlapping a preceding segment and a latter half of each segment overlapping a succeeding segment.

Selecting one of the one or more fatigue data segments may comprise randomly selecting a segment from the one or more fatigue data segments.

Setting the EEG classifier as the EEG model may comprise:
   setting the segment of maximum fatigue as a revised assumed maximum fatigue segment;
   performing step iii. using the alert state segment and revised assumed maximum fatigue segment; and
   setting the EEG classifier to be the EEG model.

Also described herein is a computing system for discriminating between alert and fatigue states in EEG data, comprising:

a model applicator module for applying an EEG model established by the computer process described above, to EEG data;
an EEG receiver for receiving a subsequently received EEG segment; and
an alert module for producing an alert if the model applicator module determines the subsequently received EEG segment is indicative of fatigue.

EEG data comprises one or more EEG segments.

The model applicator may process the subsequently received EEG segment (i.e. apply the EEG model to the subsequently received EEG segment) in real-time.

In recursively assessing each epoch or segment of EEG data, the present embodiments may avoid issues with above-mentioned fatigue assessment techniques such as, in the case of performance measurements techniques, micro-stage and early-stage of fatigue where fatigue would not be detected in the absence of poor performance, and in the case of imaging-based techniques, visible symptoms of driver fatigue that are not visible to the camera or other imaging device. Furthermore, some embodiments may accommodate changes in driver behaviour caused by subjects' experience or personality rather than fatigue, since each segment is assessed against all other segments rather than against a pre-conceived performance baseline.

BRIEF DESCRIPTION OF THE DRAWINGS

Some embodiments of the present disclosure will now be provided by way of non-limiting example only, with reference to the accompanying drawings in which:

FIG. 6 illustrates an exemplary user interface showing instructions for the performance of an alert-state test and a fatigue-state test;

FIG. 7, comprising FIGS. 7(a) and 7(b), illustrates scores generated for EEG fatigue data segments during a fatigue-state test as described with reference to FIG. 4.

DETAILED DESCRIPTION

Described is a computer process that enables a distinction to be made between alerts states and fatigue states of a subject. The computer process, and computer system implementing that process, may involve the recursive refinement of an electroencephalogram (EEG) classifier used to discriminate between alerts states and fatigue states of a subject.

The process establishes an EEG model by recursively refining an EEG classifier until further refinement appears to yield an improvement that is within a predetermined amount, or no improvement. Thus no assumption needs to be made as to when a subject is anticipated to have transitioned from an alert state to a fatigue state. The process identifies the segment illustrating the highest level of fatigue of a subject, or a segment that is very close to the highest level of fatigue, and uses that segment along with another segment illustrative of an alert state of the subject, to set the boundaries between which it is expected future EEG signals will fall.

Figure 1:
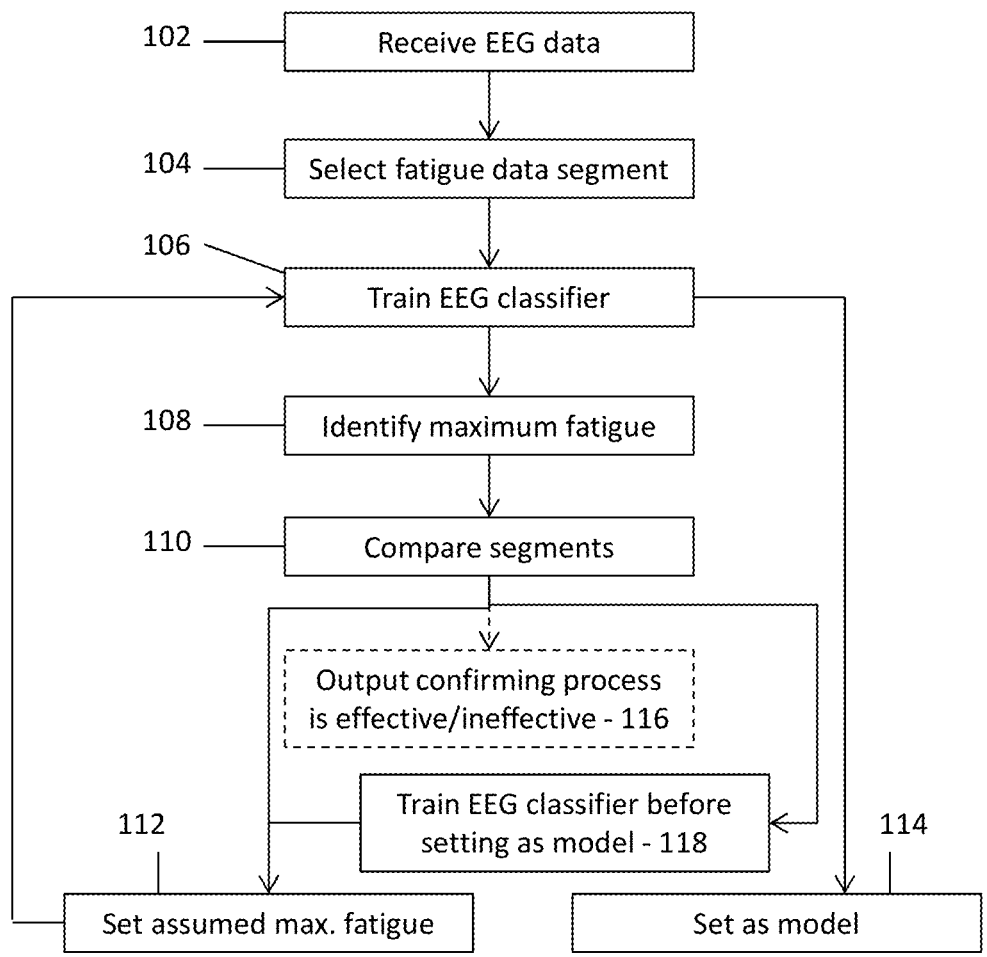
FIG. 1 illustrates a computer process for establishing an EEG model.

These advantages may be enabled by the computer process 100, as shown in FIG. 1. The computer process 100 establishes an EEG model for discriminating between alert and fatigue states. The process 100 broadly comprises:

Step 102: receiving EEG data from which an EEG classifier can be developed;
Step 104: selecting a fatigue data segment;
Step 106: training an EEG classifier;
Step 108: identify segment of maximum fatigue;
Step 110: compare segments;
Step 112: set assumed maximum fatigue segment; and
Step 114: set the EEG classifier as the EEG model.

The process 100 can recursively improve an EEG classifier to increase confidence in the ability of that classifier to discriminate between alert states and fatigue states of a subject. The process 100, when implemented in real-time, may therefore be useable to assess a driver's fatigue level and alert the driver of when they are becoming fatigued.

Step 102 of process 100 involves receiving EEG data. The data is received by receiver module 202 of system 200 shown in FIG. 2. The EEG data may be recorded directly from a subject in a known manner, or may be supplied from a database of pre-recorded EEG data. The data, once received, may be stored in receiver module database 204 of, or associated with, the receiver module 202.

The EEG data received in accordance with step 102 includes an alert state segment and one or more EEG fatigue data segments. As discussed with reference to step 106, the alert state segment and one or more EEG fatigue data segments can be used to form an EEG feature space from which the EEG classifier can be derived.

The alert state segment is illustrative of an alert state of at least one subject which may be, or include, the subject to which process 100 is being applied (the subject in question). In some cases, the alert state segment is acquired by recording EEG signals during a game designed to induce an alert state, as discussed further with reference to FIG. 4. The alert state segment may instead be artificially created EEG data. The term 'artificially created' is intended mean the data has not been recorded from the subject in question, but is instead generated to replicate what is believed to be a highly alert state of the subject in question (e.g. with reference to characteristics such as the age, fitness and gender of the subject in question) or of subjects in general. Thus artificial data may be subject-unspecific and/or derived from a pool of subjects that may or may not include the subject in question.

The one or more EEG fatigue data segments are data segments at least one of which is illustrative of a fatigue state of the at least one subject. In some cases many or all of the EEG fatigue data segments may be illustrative of a fatigue state of the at least one subject. Moreover, the EEG fatigue data segments may be recorded directly from the subject in question, and may be recorded in real-time.

The one or more EEG fatigue data segments may constitute a period of EEG data received in accordance with step 102, that is then segmented in order to produce the one or more, and presently multiple, EEG fatigue data segments. Segmenting, performed by segmenter 206, may involve simply cutting the EEG data into regular segments of a predetermined length—e.g. 2 seconds, or a length otherwise selected to match a length of the alert state segment. Segmenting may instead involve dividing the data into overlapping segments. This ensures any sharp or clear transition between an alert state and fatigue state is within a particular segment rather than on the boundary between successive segments. A first half of each segment may overlap a preceding segment and a latter, or second, half of each segment may overlap a succeeding segment. Thus each segment, with the exception of the first segment, may overlap a preceding segment by 50%—e.g. for segments of 2 seconds, the first 1 second of each segment may also be present in the preceding segment. Similarly, each segment, with the exception of the last segment, may similarly overlap a succeeding segment by 50%.

The one or more fatigue data segments are, ideally, the same length as the alert state segment. This ensures the process 100 compares feature sets of the same size and resolution, when comparing the alert state with potential fatigue states.

Step 104 involves selecting one of the one or more fatigue data segments and setting it to be an assumed maximum fatigue segment. Step 104 is performed by the segment selector 208 of computer system 200 of FIG. 2. The segment may be randomly selected from the one or more fatigue data segments. This is because the process 100 may iteratively or recursively ascertain whether the selected segment is a good approximation of the highest state of fatigue of a subject—e.g. the subject is question—or a poor approximation. If it is not a good approximation, an EEG classifier produced using the randomly selected segment may identify a better candidate segment—i.e. a segment likely to be closer to that in which the highest level of fatigue is exhibited—and the EEG classifier will be retrained or, similarly, a new EEG classifier will be produced using the better candidate segment (hereafter the segment of maximum fatigue).

For simplicity of implementation, the segment may instead be selected to be a consistent segment in a period of EEG data. For example, the selected segment may be the first segment, the last segment (which is more likely to be that which exhibits the highest level of fatigue when compared with the first segment) or the $i^{th}$ segment, where i is any whole number—e.g. the 50th segment, where i=50. The segment may also be the middle segment or, where there is an even number of segments, the earlier of the two middle segments, or the later of the two middle segments (e.g. where the one or more EEG fatigue data segments for or comprise a chronological series—note: they need not necessarily form a chronological series where step 108 does not use the order of segments in the assessment of the degree to which those segments represent a fatigue state of the subject).

Whichever method is used to select the segment from the one or more fatigue data segments, the selected segment is then set to be the assumed maximum fatigue segment. For subsequent steps, the process 100 may assume that the alert state segment and assumed maximum fatigue segment define respectively opposite ends of a fatigue spectrum. The alert state segment may define a zero baseline—i.e. no fatigue—and the assumed maximum fatigue segment may be assumed to be 1—i.e. the highest recorded fatigue segment for the subject.

Step 106 involves training the EEG classifier. This may be performed by EEG classifier trainer 210 of computer system 200 of FIG. 2, which trains the EEG classifier by extracting an EEG feature space from the alert state segment and assumed maximum fatigue segment.

The feature identifier 212 of EEG classifier trainer 210 takes the assumed maximum fatigue segment and the alert state segment and identifies features that distinguish one from the other. These features are then assumed to be capable of classifying other EEG segments as being representative of either a fatigue state or an alert state. The feature identifier 212 may use any known method for identifying relevant features, such as a linear discriminant analyser (LDA) technique.

In some instances, energy power or absolute energy power may be a feature used for discriminating between segments representing an alert state and segments representing a fatigue state. However, EEG properties vary among different subjects. The variation is particularly pronounced for features such as amplitude. The feature identifier 212 may therefore calculate the energy power ratio—e.g. the spectral power ratio for the baseline EEG segment and assumed maximum fatigue segment. Using the ratio may serve to normalize the data to produce robust and subject-independent quantity measurements of the spectrum power.

The feature identifier 212 may use temporal shifting windows of EEG data—i.e. temporal shifting segments—as the basis for identifying features for EEG classifiers. For example, temporal windows of 2 seconds, with 50% overlap, may be used to compare consecutive temporal segments. Using the overlap, each segment represents EEG data for a current period of time that is under analysis, that has a relationship with past and future data—i.e. preceding and succeeding EEG segments.

The spectral features may be extracted along the 2 second shifting window using a fast Fourier transformation (FFT).

The total power spectrum is calculated by summing up the power spectrum among the cutoff frequency bands:

$$P_{total} = \sum_{f=F_{min}}^{F_{max}} P(f) \quad (1)$$

where $P(f)$ is the power of frequency f, $F_{max}$ is the maximum frequency and $F_{min}$ is the minimum frequency. In the proposed vector of frequency bands B as set out below, $F_{max}=64$ Hz and $F_{min}=0.3$ Hz. The power ratio of each frequency band is defined as:

$$Pr(i) = \frac{\sum_{f=f_{low}(i)}^{f_{high}(i)} P(i)}{P_{total}} \quad (2)$$

where flow(i) and fhigh(i) indicate the range of the respective spectral power band.

The boundaries may be defined by a vector of frequency bands. The vector of frequency bands may be chosen so that any desired band pass definition can be determined. Moreover, the vector of frequency bands may be chosen to closely match frequency bands that facilitate identification of different mental states, or neuro-physiological symptoms, of the subject. For example, the vector of frequency bands may be B={0.3 4 6 8 12 18 30 50 64}, from which any relevant band pass definition can be determined, e.g. the flow(2)=4 Hz and fhigh(2)=6 Hz, $F_{min}=0.3$ Hz and $F_{max}=64$ Hz. In the present case, the proposed vector B was chosen after rounds of experiments attempting to identify optimal settings for feature extraction. Thus vector B, being {0.3 4 6 8 12 18 30 50 64}, closely matches the bands that plays important roles in different mental states, e.g., consciousness states Delta (0.5-4 Hz), Spindle (12-'18 Hz), Beta(12-30 Hz), Alpha (8-12 Hz) etc. In some cases the 64 Hz entry in vector B can be removed, such that it yields 7 spectral power ratios. However, in the present case the vector B yields 8 spectral power ratios Pr={pr(i)}; i=1 . . . 8. These ratios may, for example, be derived by considering vector B as an ordered list of pairs—e.g. a range defined by one pair is 0.3 Hz to 4 Hz, the range defined by the next pair is 4 Hz to 6 Hz and so on. These ratios can be further processed using spectral envelope feature extraction—i.e. the EEG feature space is based on spectral envelopes for the alert state segment and assumed maximum fatigue segment.

The concept of a spectral envelope for spectral analysis has been used in automatic speech recognition (ASR). In the context of alertness or fatigue determination, the spectral envelope is an efficient tool for exploring the periodic nature of a categorical time series with minimal, or low, loss of information.

The spectral envelope feature extraction method described herein employs envelope-based spectral filtering. The filtering process endeavours to suppress color noise appearing in the spectral power periodogram—i.e. the power spectrum of a noise signal such as white noise and Brownian noise.

To define the filter, the edge frequencies of pass and stop bands are defined. While any appropriate filter may be used—e.g. Chebyshev type I and II or Butterworth filters—the present embodiment uses a Chebyshev filter. The Chebyshev filter is given a specially defined spectral space of {0-0.5} Hz that is further divided into 2 bands in a log-space. A Chebyshev type I filter may be applied to the spectral power bands to increase frequency roll-off and passband ripple. Conversely, a Chebyshev type II filter may be applied to the 8 spectral power bands acquired from the above step, yielding another 16 parameters. The Chebyshev type II filter emphasizes stopband ripple.

The spectral parameters extracted along the shifting or sliding window (e.g. the 2 second sliding window discussed with reference to FIG. 4) exhibit a Gaussian distribution. The mean and variation of each parameter is are extracted (i.e. calculated) to form a feature space. For the abovementioned process involving extraction of spectral power ratio, spectral envelope calculation and Gaussian feature extraction may result in a feature space with 48 features—each such step will be understood by the skilled person in view of present teachings. Spectral envelope-based features, comprised of spectral powers and their spectral derivatives, form a feature space that is more discriminative than previously proposed feature sets for use in other applications such as, for example, sleep stage detection.

The feature space derived using the present teachings may identify features of difference between the alert state segment and the assumed maximum fatigue segment—i.e. features that distinguish one from the other. These features are then assumed in general to distinguish segments representing a fatigue state from those that represent an alert state. Once a new assumed maximum fatigue segment is identified in accordance with step 110, that new segment is assumed to be representative of a deeper state of fatigue than the previous assumed maximum fatigue segment. A new feature space may then be generated for the new assumed maximum fatigue segment and the alert state segment. The new feature space may therefore be a better general representation of the features that distinguish an alert state from a fatigue state, or at least a better representation of the features that distinguish an alert state from a fatigue state for the particular subject. This process can be recursively repeated until the feature space, which applied according to step 108, does not result in a fatigue data segment being identified that is inconsistent with the assumed maximum fatigue segment.

Table 1 describes the features proposed in accordance with the present embodiment. Firstly, 8 sub bands are extracted from the frequency domain. The band power of each sub band is then calculated, and the Gaussian parameters and envelope features are then obtained for each sub band. In Table 1, features 1 to 24 are the mean values, and features 25 to 48 are the standard deviation values of the filter band power and the corresponding envelope features.

TABLE 1 feature design

| Features | Description of features |
|---|---|
| 1 to 8 | Mean band power ratio of the 8 sub bands |
| 9 to 16 | Mean lower band spectral envelope feature of the 8 bands |
| 17 to 24 | Mean higher band spectral envelope feature of the 8 bands |
| 25 to 32 | Standard deviation of the power band ratio of the 8 bands |
| 33 to 40 | Standard deviation of the lower band spectral envelope of the 8 bands |
| 41 to 48 | Standard deviation of the higher band spectral envelope of the 8 bands |

Using Gaussian parameters can assist with normalising data. The result is Gaussian parameters can give a more stable, reliable and repeatable output when compared with band power. The amplitude envelope curve traces the crests and troughs of the sub band power, provide additional information reflecting EEG spectrum changes related to fatigue statues. Thus the EEG feature space comprises Gaussian parameters for the spectral power ratios and spectral envelopes as discussed with reference to Table 1.

Step 108 involves identifying a segment of maximum fatigue. This is achieved, using the maximum fatigue identifier module 214, by applying the EEG classifier to each of the fatigue data segments as discussed with reference to process 400 of FIG. 4. The EEG classifier classifies each segment as being representative of a fatigue state or an alert state. The scorer 216 then calculates a score for each segment based on the results of application of the EEG classifier to the respective segment.

For each segment the score may be, for example, a number of features from the feature set where the EEG fatigue data segment being scored scores higher than the assumed maximum fatigue segment. For example, the segment being scored may be different from the alert state segment, in a relevant feature, by an amount that is greater than the difference between the assumed maximum fatigue segment and alert state segment, in that same feature. The score may also be a count of the difference between the number of features where the segment being scored has a greater difference from the relevant feature in the alert state segment, when compared the number of features where the score has a lesser difference.

The score may instead depend on the degree of difference. For example, the difference between the assumed maximum fatigue segment and the alert state segment, in respect of a particular feature, may be considered to be a 100% difference—this may similarly be assumed for all features. An alternative fatigue data segment may produce a 95% difference for that feature, and a 125% difference for an alternative feature. Thus, the score for the alternative fatigue data segment may be 110%—i.e. (95% plus 125%) divided by 2. The alternative fatigue data segment is therefore considered more adapted to distinguish a fatigue state from an alert state, with respect to the feature space generated for the assumed maximum fatigue segment and alert state segment. Similarly, a segment may be "consistent" with the assumed maximum fatigue segment if its score is within a predetermined amount (e.g. 0%, 1%, 2%, 5% or 10%) of that of the assumed maximum fatigue segment—e.g. where the predetermined amount is 5%, the score may be within 0% to 105%. In this example, a score lower than 100% suggests the relevant segment is not a better representation of a fatigue state than the assumed maximum fatigue segment. Also, a score from 100% to 105% may be considered likely to provide an insufficient enhancement of the EEG classifier to warrant a further iteration of steps 106 onwards. A segment may also be considered "inconsistent" with the assumed maximum fatigue segment if its score is outside that predetermined amount—e.g. greater than 105%.

The segment with the highest score, or lowest score as the case may be, is then identified. Typically the highest score will be used since it enables the test scores to remain positive. In other words, if an alert state is assumed to be zero, and we have a randomly selected fatigue-state segment defining the initial high bound of a fatigue spectrum—e.g. "1"—then all other fatigue values will either fall between 0 and 1 or, if they are potentially indicative of greater fatigue than the randomly selected segment, a value higher than 1. In either case, each value for fatigue will be greater than 0. For illustrative purposes, we will therefore proceed with explaining the process 100 using the highest score, though the skilled person will appreciate a lowest score may similarly be used.

The score of the segment with the highest score is compared to the score of the assumed maximum fatigue segment—typically "1"—using segment comparator 218—step 110. The segment comparator 218 is intended to determine if the segment of maximum fatigue is inconsistent with the assumed maximum fatigue segment. If the segment of maximum fatigue is inconsistent with the assumed maximum fatigue segment, the limit setter 220 sets the segment of maximum fatigue as the assumed maximum fatigue segment (i.e. a "revised assumed maximum fatigue segment)—step 112—and steps 106 onwards are performed with the new assumed maximum fatigue segment. To make subsequent iterations of steps 106 onwards more efficient, those steps may only be performed on those segments of the one or more fatigue data segments that were determined to be illustrative of a fatigue state of the subject.

The segment of maximum fatigue and the assumed maximum fatigue segment are "inconsistent" when, for example,
  the score, as determined by scorer 216, for the assumed maximum fatigue segment is lower than the score for the segment of maximum fatigue—thus the score for the segment of maximum fatigue is a more appropriate upper bound for the fatigue spectrum; or
  where the score for the segment of maximum fatigue is greater than the score for the assumed maximum fatigue segment by a predetermined amount—i.e. a threshold difference in those scores is used to determine if the scores are sufficiently similar that further refinement of the EEG classifier will yield little gain in its ability to accurately distinguish between alert states and fatigue states. In one example, the predetermined amount is 5%—i.e. where the score for the assumed maximum fatigue segment is "1", the segment of maximum fatigue will be inconsistent if its score is 1.05 or higher—and in other examples it may be 3%, 8% or 10%.

Similarly, the assumed maximum fatigue segment and the segment of maximum fatigue identified in step 108 are "not inconsistent", or are "consistent", if their scores are the same or if the score for the segment of maximum fatigue is greater than that for the assumed maximum fatigue segment by less than the predetermined amount. The term "greater than", in the context of comparing the segment of maximum fatigue to the assumed maximum fatigue segment, may refer to the score for one segment being higher than the score for the other, or may alternatively refer to the magnitude of the score for one segment being higher than the magnitude of the score for the other. The magnitude interpretation accounts for the score for the assumed maximum fatigue segment being either the high bound of the fatigue spectrum—i.e. "1"—or the low bound—i.e. "0".

If the segment of maximum fatigue is consistent with the assumed maximum fatigue segment, the model output module 222 sets the EEG classifier as the EEG model—step 114. The EEG model can then be used for discriminating between alert and fatigue states in EEG data. In some cases, the EEG model may be programmed into a wearable piece of headgear—e.g. a headband or hat—worn by a driver to assess, in real-time, the fatigue state of the driver. Notably, there will be cases, as identified above, where the score for the segment of maximum fatigue is higher than that for the assumed maximum fatigue segment, but by less than the predetermined amount. In these cases, and in line with dummy step 118 of FIG. 1, while steps 108, 110 may be avoided, the model output module 222 may nevertheless use the limit setter 220 to set the segment of maximum fatigue as the assumed maximum fatigue segment (step 112), train the EEG classifier using EEG classifier trainer 210 (step 106), and set the resulting EEG classifier as the EEG model since this will be a marginal improvement on the previous model.

In this sense, an EEG classifier is also an EEG model. However, the efficacy of that classifier for use in discriminating between alert and fatigue states in new—i.e. subsequently received—EEG data is not yet known. Once it has been confirmed, e.g. by process 100, that the EEG classifier is an effective model (i.e. it passes step 110) then it is set as the EEG model for later use. Thus an EEG model is an EEG classifier that has been confirmed, through a process described herein with reference to the figures, to be effective in discriminating between alert and fatigue states in EEG data.

Steps 102, 104, 106, 108 and 110 may also be used in a computer process for determining the efficacy of an EEG classifier for discriminating between alert and fatigue states—i.e. the ability of the EEG classifier to serve as an EEG model. In particular, after performing steps 102, 104, 106 and 108, step 110 may involve determining whether the EEG classifier is effective for discriminating between alert and fatigue states by determining a score for the segment of maximum fatigue. If that score is inconsistent with a score for the assumed maximum fatigue segment, then the computer process 100—e.g. using effectiveness output module 224—outputs a confirmation that the EEG classifier is ineffective—step 116—i.e. is not an accurate discriminator of alert and fatigue states of a subject. Again, "inconsistent" will be determined in some cases as one score being exclusively greater than another, and in other cases as one score being greater than then other by at least a predetermined amount. Conversely, if that score for the segment of maximum fatigue is consistent with a score for the assumed maximum fatigue segment, then the computer process 100, using effectiveness output module 224, outputs a confirmation that the EEG classifier is effective—step 116—i.e. is an accurate (i.e. suitably accurate or accurate enough for real-time usage in determining alert or fatigue states of a subject) discriminator of alert and fatigue states of a subject.

The computer system 200 comprises two main components. The first is a model assessor 201 that performs steps 102 to 114, or step 116 depending on the desired application of the model assessor 201. These components may be integral or separate. The second is a discriminator system 226 that receives the EEG model outputted by model output module 222. The discriminator system 226 uses the model applicator module 230 to discriminate between alert and fatigue states in EEG data by using the EEG model outputted by model output module 222 to assess whether subsequently received EEG data—e.g. a subsequently received EEG segment—is illustrative of a fatigue data segment or an alert data segment. If the subsequently received EEG segment is illustrative of a fatigue data segment then alert 232 generates an alert. The alert is generated to warn the subject, from which the subsequent EEG segment was measured, that they are experiencing fatigue.

The discriminator system 216 comprises EEG receiver 228 for receiving the subsequent EEG data—i.e. the subsequently received EEG data mentioned above. The EEG receiver 228 may comprise one or more EEG sensors, or may be in communication with one or more EEG sensors. For example, the discriminator system 216 may comprise a smartphone and the one or more EEG sensors may be installed in an EEG sensor device—e.g. a piece of headgear such as a cap, headband or hat—in communication (e.g. via hardwired or Bluetooth connection) with that smartphone. The headgear sends EEG signals, comprising one or more EEG data segments, to the smartphone. The smartphone then assesses (using model applicator module 230) whether each EEG data segment is illustrative of a fatigue data segment or an alert data segment. If an EEG data segment is illustrative of a fatigue data segment, then the smartphone issues an alert—e.g. an audible alert through a speaker of the smartphone or a visual alert on a display of the smartphone.

In another example, the discriminator system 216 may comprise the EEG sensor device—e.g. the EEG sensor device may be mounted in the cap, headband or hat.

The alert may be generated through an alert module 232. The alert module 232 produces the alert if the model applicator module 230 determines the subsequently received EEG segment is indicative of fatigue.

In some embodiments, the discriminator system 226 displays an alert-state test and fatigue-state test to the subject—the alert-state test and fatigue-state test are described with reference to FIG. 4. The EEG receiver 228 receives EEG data (e.g. the alert state segment, one or more EEG fatigue data segments and/or the subsequently received EEG data) acquired during performance of those tests—e.g. directly, during performance of the tests or from a database comprising pre-recorded EEG data acquired during performance of the tests (e.g the alert state segment and/or the one or more EEG fatigue data segments). The EEG receiver 228 may thus deliver the alert state segment and one or more EEG fatigue data segments to the receiver module 202—for producing the EEG model—or the EEG receiver 228 and receiver module 202 may be a single receiver.

In some embodiments, the model assessor 201 and discriminator system 226 form a single device—e.g. a smartphone.

Figure 3:
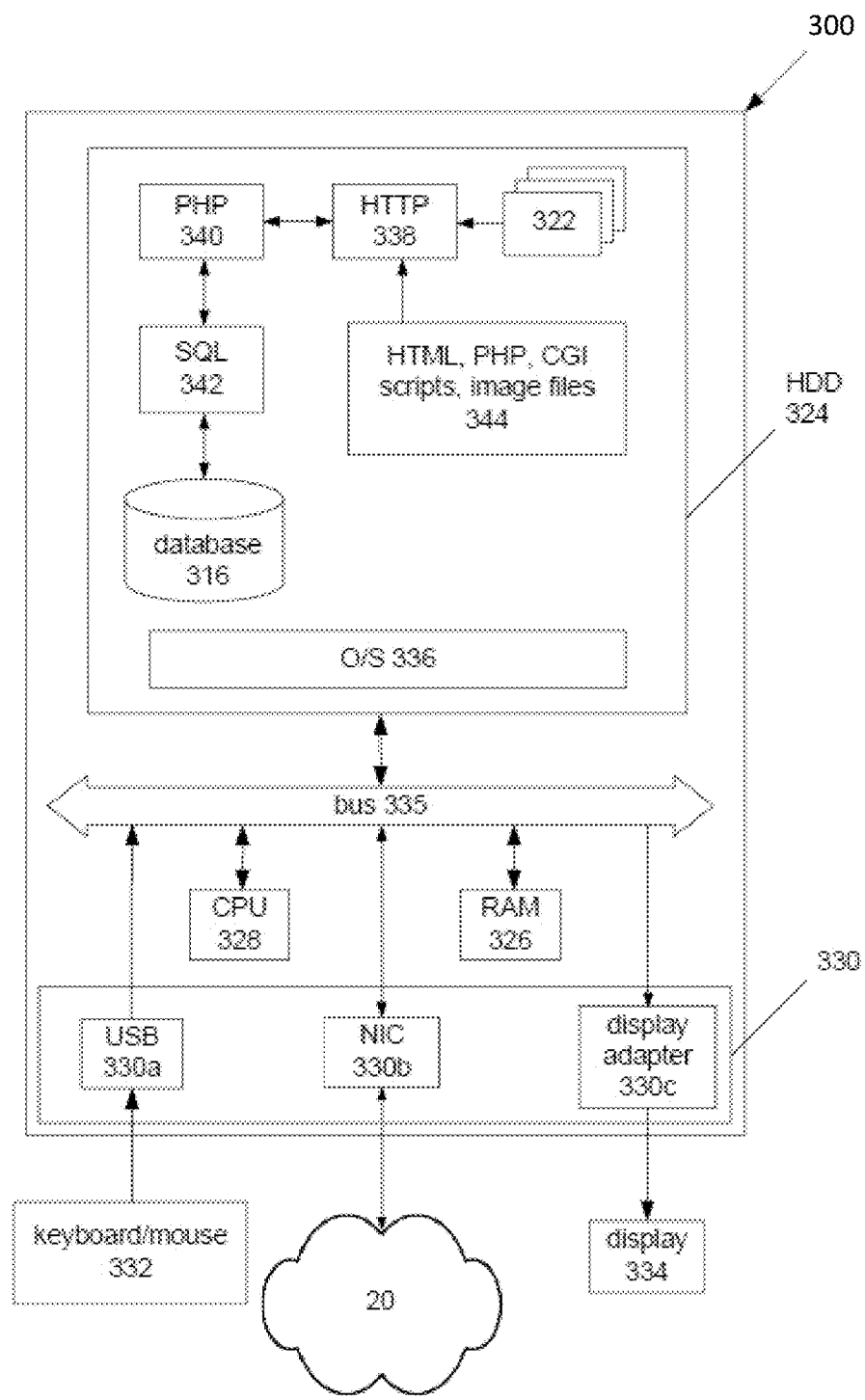
FIG. 3 is a schematic diagram of a computer system for implementing the process of FIG. 1.

FIG. 3 shows an example computing system 300. The computer system 300 may be capable of implementing the model assessor 201, the discriminator system 226, or both the model assessor 201 and discriminator system 226. In some embodiments, each component of the system 300 comprises multiple servers in communication with each other, for example over a local area network or a wide-area network such as the Internet. In other embodiments, all such components form a single device, or a single device communicatively coupled to an EEG sensor device. Where communication between devices is necessary, the may communicate over wireless communications network 20 using standard communication protocols.

The components of the computing device 300 can be configured in a variety of ways. The components can be implemented entirely by software to be executed on standard computer server hardware, which may comprise one hardware unit or different computer hardware units distributed over various locations, some of which may require the communications network 20 for communication. A number of the components or parts thereof may also be implemented by application specific integrated circuits (ASICs) or field programmable gate arrays.

In the example shown in FIG. 3, the computing device 300 is a commercially available computer system—e.g. a smartphone—based on a 32 bit or a 64 bit Intel architecture, and the processes and/or methods executed or performed by the computing device 300 are implemented in the form of programming instructions of one or more software components or modules 322 stored on non-volatile (e.g., hard disk) computer-readable storage 324 associated with the computing device 300. At least parts of the software modules 322 could alternatively be implemented as one or more dedicated hardware components, such as application-specific integrated circuits (ASICs) and/or field programmable gate arrays (FPGAs).

The computing device 300 includes at least one or more of the following standard, commercially available, computer components, all interconnected by a bus 335:
(a) random access memory (RAM) 326;
(b) at least one computer processor 328, and
(c) external computer interfaces 330:
 (i) universal serial bus (USB) interfaces 330a (at least one of which is connected to one or more user-interface devices, such as a keyboard, a pointing device (e.g., a mouse 332 or touchpad),
 (ii) a network interface connector (NIC) 330b which connects the computing device 300 to a data communications network, such as the wireless communications network 20; and
 (iii) a display adapter 330c, which is connected to a display device 334 such as a liquid-crystal display (LCD) panel device.

The computing device 300 includes a plurality of standard software modules, including:
(a) an operating system (OS) 336 (e.g., Linux or Microsoft Windows);
(b) web server software 338 (e.g., Apache, available at http://www.apache.org);
(c) scripting language modules 340 (e.g., personal home page or PHP, available at http://www.php.net, or Microsoft ASP); and
(d) structured query language (SQL) modules 342 (e.g., MySQL, available from http://www.mysql.com), which allow data to be stored in and retrieved/accessed from an SQL database 316.

Advantageously, the database 316 forms part of the computer readable data storage 324. Alternatively, the database 316 is located remote from the server 14 shown in FIG. 3.

Together, the web server 338, scripting language 340, and SQL modules 342 provide the computing device 300 with the general ability to allow the other components of the system 10 to communicate with the system 300 and in particular to provide data to and receive data from the database 316. It will be understood by those skilled in the art that the specific functionality provided by the computing device 300 to such users is provided by scripts accessible by the web server 338, including the one or more software modules 322 implementing the processes performed by the computing device 300, and also any other scripts and supporting data 344, including markup language (e.g., HTML, XML) scripts, PHP (or ASP), and/or CGI scripts, image files, style sheets, and the like.

The boundaries between the modules and components in the software modules 322 are exemplary, and alternative embodiments may merge modules or impose an alternative decomposition of functionality of modules. For example, the modules discussed herein may be decomposed into submodules to be executed as multiple computer processes, and, optionally, on multiple computers. Moreover, alternative embodiments may combine multiple instances of a particular module or submodule. Furthermore, the operations may be combined or the functionality of the operations may be distributed in additional operations in accordance with the invention. Alternatively, such actions may be embodied in the structure of circuitry that implements such functionality, such as the micro-code of a complex instruction set computer (CISC), firmware programmed into programmable or erasable/programmable devices, the configuration of a field-programmable gate array (FPGA), the design of a gate array or full-custom application-specific integrated circuit (ASIC), or the like.

Each of the blocks of the processes of the computing device 300 may be executed by a module (of software modules 322) or a portion of a module. The processes may be embodied in a non-transient machine-readable and/or computer-readable medium for configuring a computer system to execute the method. The software modules may be stored within and/or transmitted to a computer system memory to configure the computer system to perform the functions of the module.

The computing device 300 normally processes information according to a program (a list of internally stored instructions such as a particular application program and/or an operating system) and produces resultant output information via input/output (I/O) devices 330. A computer process typically includes an executing (running) program or portion of a program, current program values and state information, and the resources used by the operating system to manage the execution of the process. A parent process may spawn other, child processes to help perform the overall functionality of the parent process. Because the parent process specifically spawns the child processes to perform a portion of the overall functionality of the parent process, the functions performed by child processes (and grandchild processes, etc.) may sometimes be described as being performed by the parent process.

In order to model a subject's descent into a state of fatigue, some binary data is required to form the model—e.g. data representing both fatigue states and alert states of a subject.

In the context of EEG data, an alert state will be represented by an alert state segment—a segment of EEG data representative of a subject that is alert at the time the EEG data is recorded. An alert state segment may alternatively be artificial data (i.e. data that is not recorded from a subject) assumed to be consistent with such EEG data. Such data can be generated based on characteristic EEG signals that are anticipated to illustrate an alert state.

Similarly, a fatigue state is represented by a fatigue state segment. A fatigue state may be assumed to be present in EEG data taken from a subject during performance of a test designed to induce fatigue.

Thus, to derive alert state EEG data and fatigue state EEG data, two experiments are designed—an alert-state test and a fatigue-state test. In the alert-state test, subject(s) are required to perform intensive tasks to keep them highly alert. The duration of the alert-state test is short so the tasks end before the subject(s) become bored. In the fatigue-state test, it is assumed that fatigue is a gradual process with a potentially poorly designed transition phase from an alert-state to a fatigue-state of the subject. The fatigue-state test may involve lengthy, repetitive, fatigue-inducing tasks in, for example, a driver simulator environment. The fatigue-state test is run to ensure each subject falls into a fatigue-state, or even a sleep state, during the test. Present embodiments then locate, from all the EEG data acquired during the fatigue-state test, a segment illustrative of a high level of fatigue and, ideally, the segment illustrating the highest level of fatigue.

Figure 4:
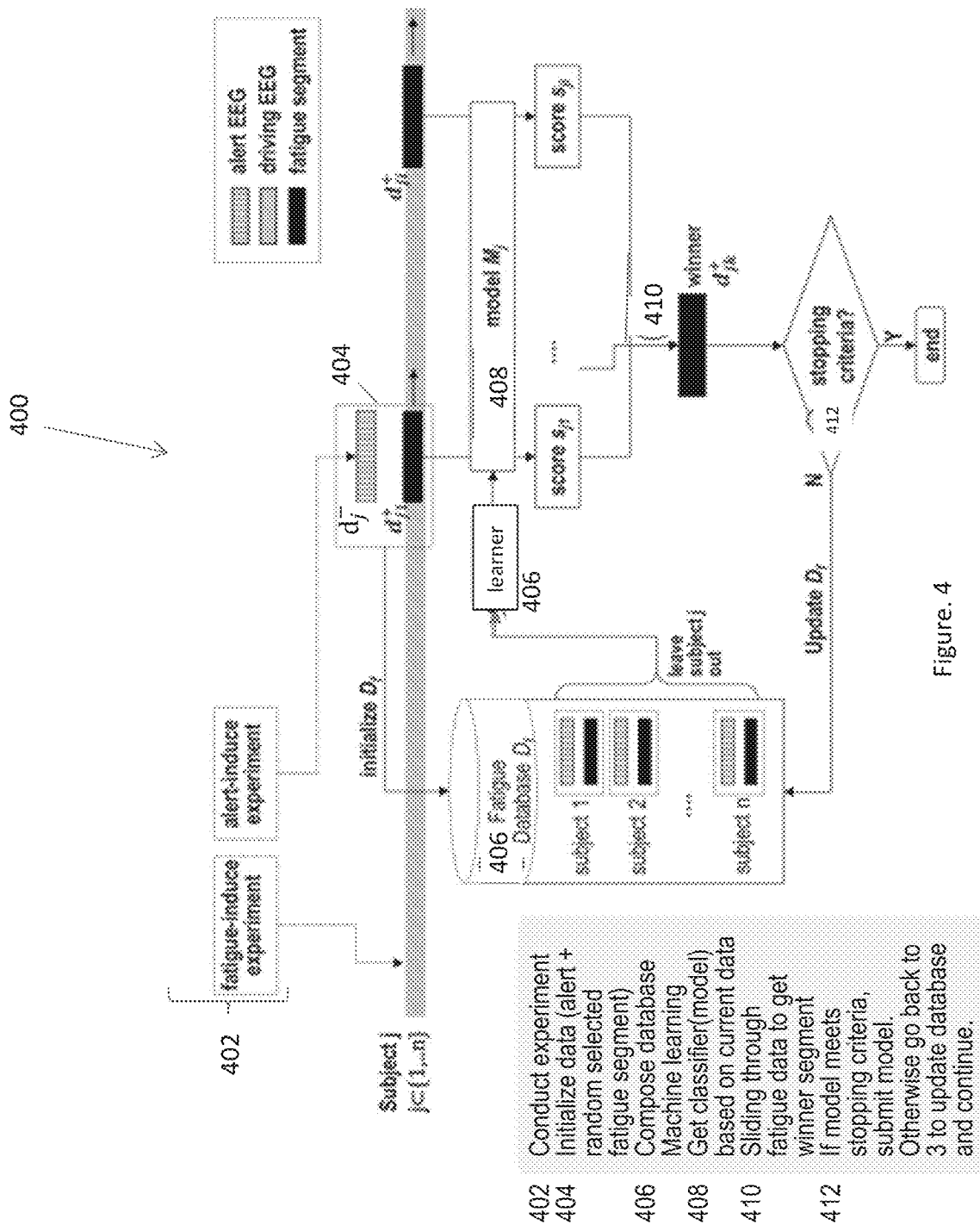
FIG. 4 illustrates a process for producing an EEG model.

FIG. 4, illustrates a process 400 for selecting segments by which to generate an EEG model for discriminating between fatigue and alert states of a subject. As per process 100, one goal of process 400 is, for each subject to whom the test is applied, to search for the segment representing highest fatigue $d_{jk}$+ from a pool of segments $D^+=\{d_1^+, d_2^+, \ldots d_n^+\}$. For these variables, the "+" sign refers to EEG data, or segments, taken during a fatigue-inducing test, and the "−" sign refers to EEG data, or segments, taken during an alert-state test.

Firstly, step 402 involves forming a pool of EEG data segments. An alert-state test and a fatigue-state test are performed for each subject. The alert state segment used in steps 106 onwards, of process 100, may comprise all EEG data measured during the alert-state test—i.e. the alert-state test may be one segment long. A pool of segments is then composed using a sliding window moved along EEG signals measured during the lengthy fatigue-inducing driving experiment—i.e. a fatigue-state test. To ensure the EEG model is balanced, the windows (i.e. segment) extracted for the alert-state test have equal size to those extracted for the fatigue-state test—i.e., $d_j^-$ and $d_{ji}^+$ have the same length.

A sampling space is then formed (step 404) using:
EEG data $d_j^-$, $j \subset \{1, \ldots n\}$ acquired from the alert experiment, where n is the number of subjects; and
a segment of EEG data $d_{ji}^+$, $i \subset \{1, \ldots m\}$ is selected from a fatigue-state test (e.g. a driving experiment) in accordance with step 104.

In particular, a segment may be selected from the driving data (i.e. fatigue-state test data) at a point assumed to be indicative of fatigue. For example, the middle point of the driving data may be a point at which a fatigue state has been induced for a while, and thus is indicative of fatigue. In some embodiments, the segment representing the highest state of fatigue (i.e. the segment during which the driver was most fatigued) may be assumed to be in the latter half of the fatigue-state test EEG data, and thus the process 400 runs only on the latter half of that data. In other embodiments, process 400 may run on the full period of EEG data—e.g. all the data acquired for the fatigue-state test.

A fatigue database, $D_f$, is then initialised (step 406), to store the pairs of data $D=\{D_1, D_2, \ldots, D_n\}$, where $D_i=\{d_i^-, d_i^+\}$, $i=1, \ldots n$ from all subjects.

Figure 2:
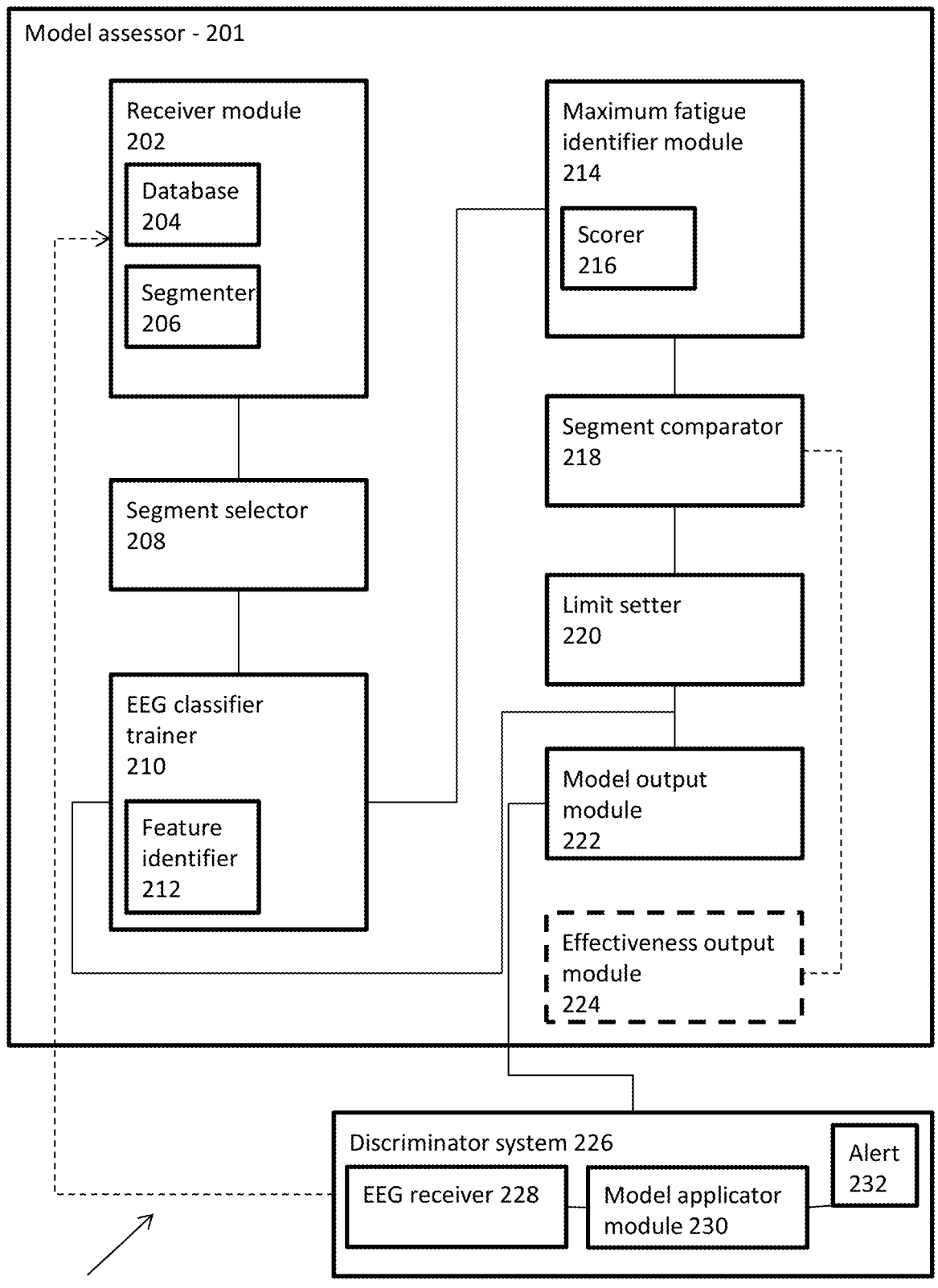
FIG. 2 is a schematic diagram showing function system modules for executing the process of FIG. 1.

A feature identifier (see feature identifier 212 of the EEG classifier trainer 210 of the computer system 200 of FIG. 2), or learner, then identifies a group of features that can be used to separate segments in the fatigue-state test data into segments representative of an alert state of the subject(s) and segments representative of a fatigue-state of the subject(s)—step 408. The learner can be any machine learning algorithm for identifying features that distinguish one set of data (the alert-state segment) from another set of data (the selected fatigue-state segment), such as a support vector machine (SVM), linear discriminant analyser (LDA), artificial neural network (ANN), a k-nearest neighbours approach (KNN) and so forth. In the context of the present teachings, the skilled person will understand the use of machine learning algorithms to identify feature sets for classifying input data into two or more subsets of data.

Once the group of features is identified in accordance with step 408, a group of EEG classifiers (which may be one EEG classifier in the case only a single subject is tested) can be trained using that group of features—step 410. The group of EEG classifiers may be trained using a leave-one-out approach, e.g., model for subject 1 will be trained using data from $D_f$ excluding subject 1's data. This ensures that the data for subject 1 does not unreasonably dominate or influence the process 100, 400.

The candidate fatigue segment pool $D^+=\{d_1^+, d_2^+, \ldots d_n^+\}$—i.e. the pool of segments that will be scored to identify the segment of maximum fatigue per step 108 of process 100—is then established and each candidate fatigue segment is scored by scorer 216 of maximum fatigue identifier module 214 of computer system 200 of FIG. 2—step 412. This may be achieved by sliding a window along the second half of fatigue-state test data, or using any other desired analysis method. Again, while the entire data set may be used, using the second half of the data is highly likely to capture the segment of highest fatigue while avoiding unnecessarily processing half of the data in each iteration of the process (e.g. steps 106 onwards of process 100). A score is calculated for each segment based on model $M_j$, the winning segment $d_{jk}$+—the segment of maximum fatigue for each respective subject—being determined to be that with the highest score or lowest score. In the present context, the segment of highest fatigue is the high bound "1" of the desired EEG model, and the alert state is the baseline or lower bound "0" of the EEG model. Thus the winning segment $d_{jk}$+ will be that with the highest score, based on the later-state segment derived for the specific subject and the fatigue-state data derived for all subjects minus the subject in question.

If the "stopping criteria" are met, the process 400 exits—step 414. In the context of process 100, the stopping criteria (which, though appearing to be a plural indefinite noun, will nevertheless be understood to include a single stopping criterion as required in any particular application) are tested at step 110 to determine if the segment of maximum fatigue is inconsistent with the assumed maximum fatigue segment. Relevant steps of process 400—corresponding to steps 106 to 110 of process 100, and 112 and 114 as needed—are applied to all subjects, iteratively or recursively (which, in the present context, will both simply mean that various steps are repeated until a desired outcome is reached) for as many rounds as necessary until the result meets those stopping criteria. At this point, any further iterations of steps of process 400 will not improve the resultant EEG model significantly.

Figure 5:
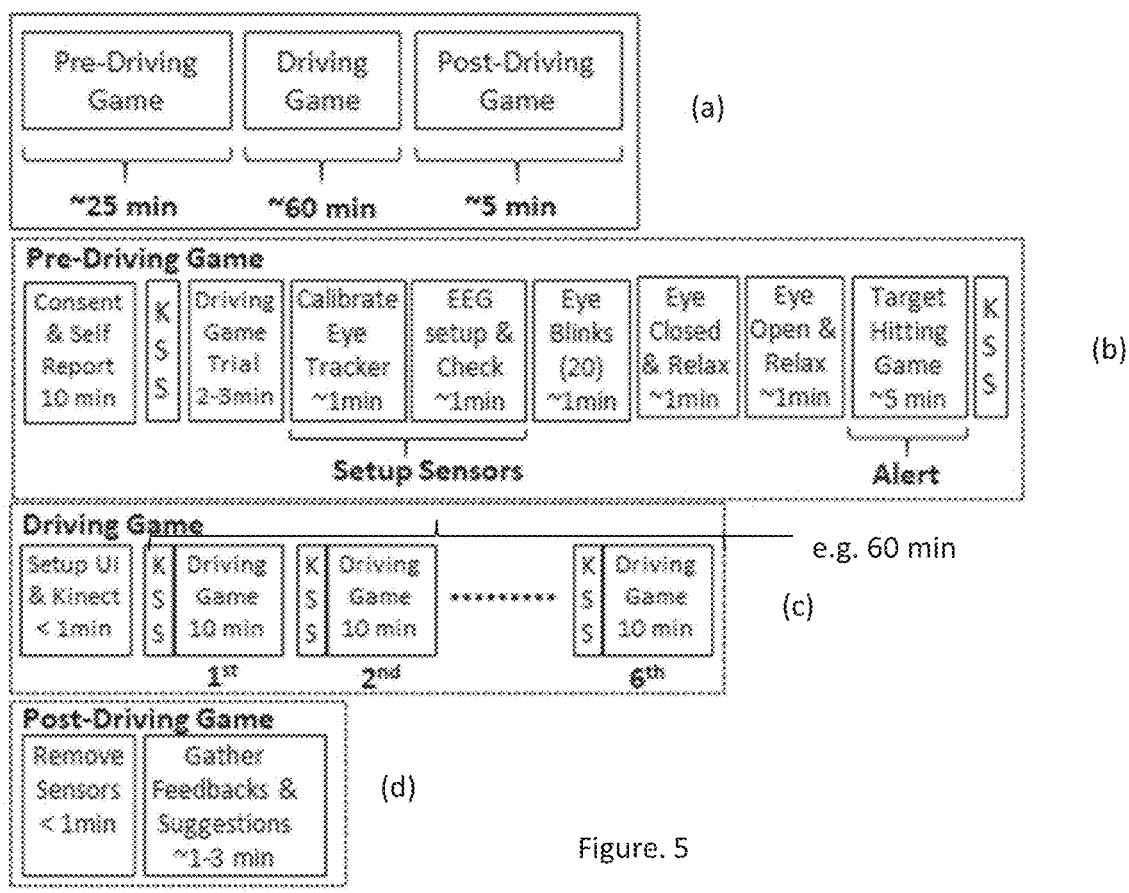
FIG. 5 illustrates a test protocol for performing the alert-state test and fatigue-state test described with reference to FIG. 4.

FIG. 5 shows the design of a fatigue test such as that discussed with reference to process 400. The test comprises a protocol as set out in part (a) of FIG. 5, to ensure proper setup of the fatigue-state test.

The protocol comprises a pre-driving game—i.e. pre-fatigue-state test—phase (b). During this phase, the subject checks-into the test e.g. by giving consent for the test to be conducted. An eye tracker and EEG sensor are then calibrated and checked to ensure proper functioning. An alert state test is then conducted, presently comprising a target-hitting game. The target-hitting game is of 5 minutes' duration and designed to maintain the subject in an alert state. The alert state segment is extracted from the EEG data recorded for the alert-state test.

After performance of the pre-driving phase (b), the protocol moves into the fatigue inducing, driving phase (c). During this phase various periods of a driving scenario are presented to the subject. The periods are designed to induce fatigue—e.g. may display a straight, open, feature-less road along which the subject must guide a vehicle. EEG fatigue data comprising one or more, and most likely a large number of, fatigue-state segments of EEG data is acquired throughout the driving phase (c).

During phase (c) the subject will sit on a driving seat in front of a computer screen, wearing an EEG headband or other EEG sensor device as mentioned above. Various sensor devices may be used for this phase, such as the Muse v2014 headband, Tobii EyeX and Microsoft Kinect V2.

FIG. 6 is an illustrative set of instructions provided to a subject for performing the test protocol set out in FIG. 5. The skilled person will appreciate the instructions may differ depending on the setup of the test—e.g. driving simulation, flying simulation—the desired amount of data to be collected, and the nature of sensors used to collect that data— e.g. eye trackers, EEG sensors, head position sensors etc.

The post-driving phase (d) involves the collection of feedback and the removal of sensors etc from the subject.

FIG. 7 shows two sets of fatigue scores for EEG fatigue data taken over a 1-hour fatigue-state test in accordance with phase (c) of FIG. 5. The differences in figures illustrate that linear descension into a fatigue state cannot be assumed. In FIG. 7(a) the subject's fatigue score was low in the first two-thirds of the driving period. The score becomes higher during the last 10 minutes of the driving period. in FIG. 7(b) a different subject undertook the fatigue-state test. The different subject was alert during the first half of the test and then rapidly entered a fatigue state during the second half of the test.

In each case, the segment of highest fatigue was in the second half of the test.

Figure 8:
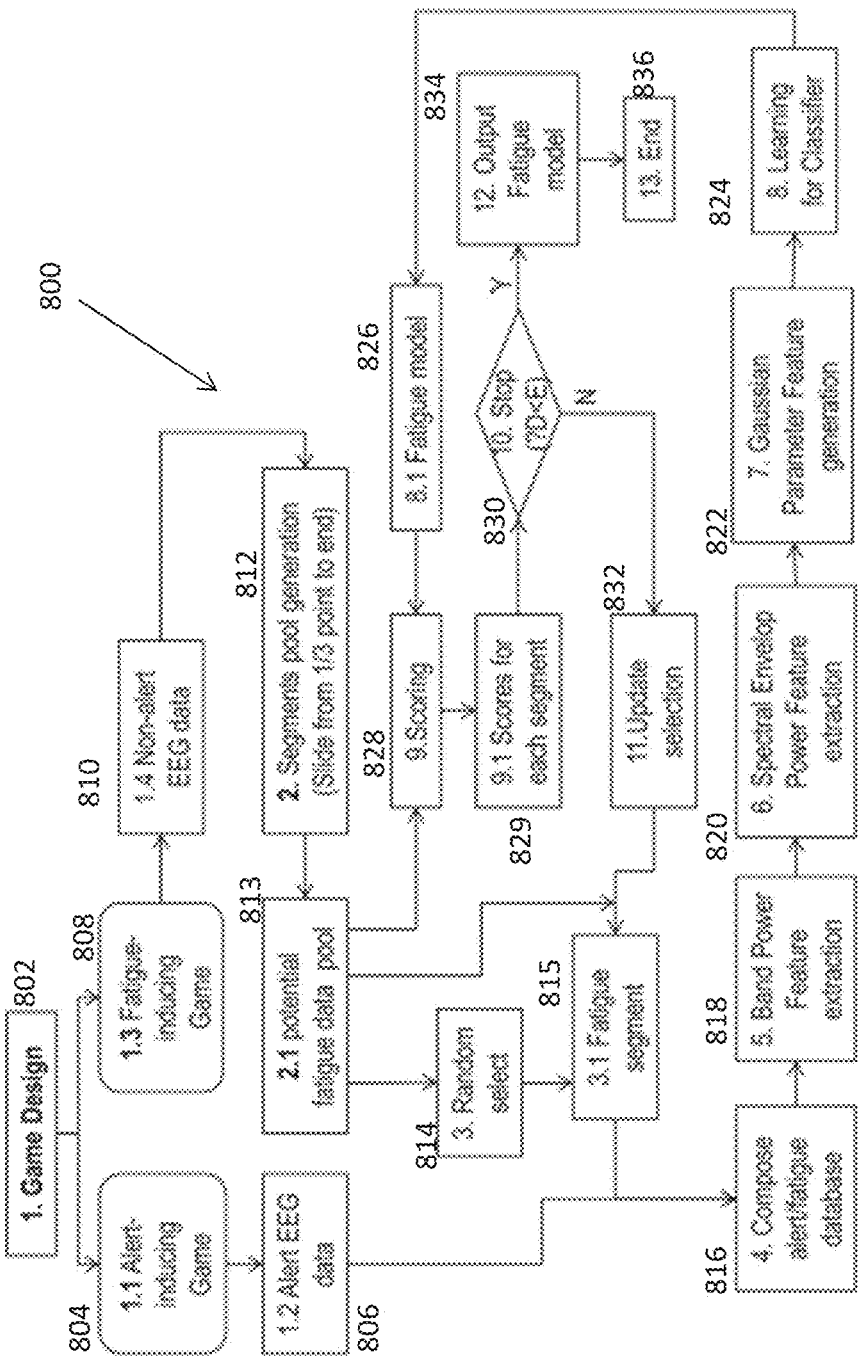
FIG. 8 is a flowchart of a process for acquiring and analysing alert and fatigue EEG data, to produce an EEG model.

Lastly, FIG. 8 illustrates a process flow 800 for implementing a computer process according to FIGS. 1, 4 and 5. The process flow 800 comprises:

802: a game design phase in which an alert-state game and a fatigue-state game are designed, per phases (b) and (c) of FIG. 5 respectively;
804: the alert-state game is then performed by a subject;
806: alert EEG data is collected during performance of the alert-state game;
808: the fatigue-state game is similarly performed by the subject, to induce fatigue and enable acquisition of potential fatigue EEG data;
810: non-alert EEG data, or fatigue EEG data (which will be taken to include potential fatigue data), is acquired;
812: a pool of potential fatigue data segments is produced from the data acquired under step 810, forming a potential fatigue data pool
813. These segments are referred to as one or more EEG fatigue data segments with reference to FIG. 1. Each EEG fatigue data segment has a similar length to the EEG data acquired during step
806—e.g. for a 5 minute alert-state test, the fatigue-state test data may be segmented into 5 minute segments;
814: a EEG fatigue data segment is randomly selected per step 104 and set as the fatigue segment (i.e. assumed maximum fatigue segment) 815;
816: an alert/fatigue database is initialized using the data produced at steps 806 and 814;
818: band power or band power ratio feature extraction is then performed as discussed with reference to FIG. 4;
820: spectral envelope features are then extracted on top of the band power features extracted at step 818;
822: Gaussian parameters are then obtained from the band power ratio features extracted at step 818 and the spectral envelope features extracted at step 820, to form a feature space;
824: the feature space is analysed using a machine learning algorithm, as discussed with reference to step 406 of the process 400 of FIG. 4;
826: the features identified by the machine learning algorithm are then used to train an EEG classifier per step 106;
828: scores are calculated by scorer 216, for each subject's fatigue data pool and each respective segment— 829;
830: the scores are checked against relevant stopping criteria as discussed with reference to step 110 of process 100 of FIG. 1;
832: if the stopping criteria are not met, the randomly selected segment is replaced with the segment of highest score and steps 816 to 830 are repeated;
834: if the stopping criteria are met, the fatigue model is outputted; and
836: the process ends.

The processes illustrated above provide a novel process for searching fatigue EEG data using a reliable 'alert' label—i.e. an EEG classifier trained using an EEG fatigue segment representative of a fatigue state of a subject—to acquire an optimal EEG model for fatigue modelling.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that the prior art forms part of the common general knowledge.

The invention claimed is:

1. A computer system for establishing an electroencephalogram (EEG) model for discriminating between alert and fatigue states, comprising:
a receiver module for receiving:
an alert state segment illustrative of an alert state of at least one subject; and
one or more EEG fatigue data segments illustrative of a fatigue state of the at least one subject;
a segment selector for selecting one of the one or more fatigue data segments and setting it to be an assumed maximum fatigue segment;
an EEG classifier trainer for training an EEG classifier by extracting an EEG feature space from the alert state segment and assumed maximum fatigue segment based on the alert state segment and assumed maximum fatigue segment defining respectively opposite ends of a fatigue spectrum;
a maximum fatigue identifier module for identifying a segment of maximum fatigue by applying the EEG classifier to each of the fatigue data segments;
a segment comparator for determining if the segment of maximum fatigue is consistent with the assumed maximum fatigue segment;

a limit setter for:
  setting the segment of maximum fatigue as a revised assumed maximum fatigue segment, if the segment of maximum fatigue is inconsistent with the assumed maximum fatigue segment; and
  supplying the EEG classifier trainer with the revised assumed maximum fatigue segment, and using the EEG classifier trainer to train the EEG classifier by extracting an EEG feature space from the alert state segment and revised assumed maximum fatigue segment based on the alert state segment and revised assumed maximum fatigue segment defining respectively opposite ends of a fatigue spectrum; and
a model output module for setting the EEG classifier as the EEG model for discriminating between alert and fatigue states in segments of EEG data.

2. The computer system of claim 1, further comprising a discriminator system configured to apply the EEG model to determine if one or more subsequently recorded EEG segments are each representative of a fatigue state or an alert state.

3. The computer system of claim 1, wherein the EEG classifier is configured to extract the EEG feature space by calculating spectral power ratios for the alert state segment and assumed maximum fatigue segment.

4. The computer system of claim 3, wherein the EEG classifier is configured to extract the EEG feature space by calculating spectral envelopes for the alert state segment and assumed maximum fatigue segment.

5. The computer system of claim 4, wherein the EEG classifier is configured to calculate Gaussian parameters for the spectral power ratios and spectral envelopes.

6. The computer system of claim 1, wherein the maximum fatigue identifier comprises a scorer configured to determine a score for each of the one or more EEG fatigue data segments, and the segment comparator is configured to determine that the maximum fatigue is inconsistent with the assumed maximum fatigue segment if:
  the score for the segment of maximum fatigue is greater than that for the assumed maximum fatigue segment; or
  the score for the segment of maximum fatigue is greater than the score for the assumed maximum fatigue segment by at least a predetermined amount.

7. The computer system of claim 1, further comprising a segmenter, the receiver module being configured to receive the one or more EEG fatigue data segments by receiving a period of EEG fatigue data and segmenting the EEG fatigue data into the one or more EEG fatigue data segments using the segmenter.

8. The computer system of claim 1, wherein the segmenter is configured to segment the EEG fatigue data into overlapping segments, a first half of each segment overlapping a preceding segment and a latter half of each segment overlapping a succeeding segment.

9. A computer process for establishing an electroencephalogram (EEG) model for discriminating between alert and fatigue states, comprising:
  i. receiving:
    an alert state segment illustrative of an alert state of at least one subject; and
    one or more EEG fatigue data segments illustrative of a fatigue state of the at least one subject;
  ii. selecting one of the one or more fatigue data segments and setting it to be an assumed maximum fatigue segment based on the alert state segment and assumed maximum fatigue segment defining respectively opposite ends of a fatigue spectrum;
  iii. training an EEG classifier by extracting an EEG feature space from the alert state segment and assumed maximum fatigue segment;
  iv. identifying a segment of maximum fatigue by applying the EEG classifier to each of the fatigue data segments;
  v(1). if the segment of maximum fatigue is inconsistent with the assumed maximum fatigue segment:
    setting the segment of maximum fatigue as the assumed maximum fatigue segment; and
    performing steps iii. to v.; and
  v(2). if the segment of maximum fatigue is consistent with the assumed maximum fatigue segment, setting the EEG classifier as the EEG model for discriminating between alert and fatigue states in EEG data.

10. A computer process according to claim 9, wherein a length of the alert state segment and the assumed maximum fatigue segment are the same.

11. A computer process according to claim 1, wherein the EEG feature space is based on spectral power ratios for the alert state segment and assumed maximum fatigue segment.

12. A computer process according to claim 11, wherein the EEG feature space is based on spectral envelopes for the alert state segment and assumed maximum fatigue segment.

13. A computer process according to claim 9, wherein the EEG classifier is used to determine a score for each of the one or more EEG fatigue data segments, and the maximum fatigue is inconsistent with the assumed maximum fatigue segment if:
  the score for the segment of maximum fatigue is greater than that for the assumed maximum fatigue segment; or
  the maximum fatigue is greater than the assumed maximum fatigue segment by at least a predetermined amount.

14. A computer process according to claim 9, wherein receiving one or more EEG fatigue data segments comprises receiving a period of EEG data and segmenting the EEG fatigue data into the one or more EEG fatigue data segments.

15. A computer process according to claim 14, wherein segmenting the EEG fatigue data into the one or more EEG fatigue data segments comprises segmenting the EEG fatigue data into overlapping segments, a first half of each segment overlapping a preceding segment and a latter half of each segment overlapping a succeeding segment.

16. A computer process according to claim 9, wherein selecting one of the one or more fatigue data segments comprises randomly selecting a segment from the one or more fatigue data segments.

17. A computer process according to claim 9, wherein setting the EEG classifier as the EEG model comprises:
  setting the segment of maximum fatigue as a revised assumed maximum fatigue segment;
  performing step iii. using the alert state segment and revised assumed maximum fatigue segment; and
  setting the EEG classifier to be the EEG model.

18. A computing system for discriminating between alert and fatigue states in EEG data, comprising:
  a model applicator module for applying an EEG model established by the computer process of claim 9, to EEG data;
  an EEG receiver for receiving a subsequently received EEG segment; and
  an alert module for producing an alert if the model applicator module determines the subsequently received EEG segment is indicative of fatigue.

* * * * *